United States Patent
Schaeffer

(10) Patent No.: US 9,681,888 B2
(45) Date of Patent: Jun. 20, 2017

(54) WIREGUIDE SET FOR CHANGING ACCESS SITES

(71) Applicant: COOK MEDICAL TECHNOLOGIES LLC, Bloomington, IN (US)

(72) Inventor: Jeremy R. Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 988 days.

(21) Appl. No.: 13/868,492

(22) Filed: Apr. 23, 2013

(65) Prior Publication Data

US 2013/0282036 A1    Oct. 24, 2013

Related U.S. Application Data

(60) Provisional application No. 61/636,943, filed on Apr. 23, 2012.

(51) Int. Cl.
*A61B 17/3207* (2006.01)
*A61B 17/34* (2006.01)
*A61M 25/09* (2006.01)
*A61M 25/00* (2006.01)
A61B 17/22 (2006.01)

(52) U.S. Cl.
CPC ...... *A61B 17/3403* (2013.01); *A61B 17/3207* (2013.01); *A61M 25/0068* (2013.01); *A61M 25/09* (2013.01); *A61M 25/09041* (2013.01); *A61B 2017/22042* (2013.01); *A61B 2017/22049* (2013.01); *A61B 2017/22094* (2013.01); *A61M 2025/09175* (2013.01)

(58) Field of Classification Search
CPC ...... A61B 17/3403; A61B 2017/22049; A61B 2017/22042; A61B 2017/22094; A61M 25/09; A61M 25/0068; A61M 25/09041; A61M 2025/09175; A61M 25/0069; A61M 25/0074; A61M 2025/0079; A61M 25/0097; A61M 25/0169
USPC ........................................................ 606/200
See application file for complete search history.

(56) References Cited

U.S. PATENT DOCUMENTS

| | | |
|---|---|---|
| 5,191,888 A | 3/1993 | Palmer et al. |
| 5,511,559 A | 4/1996 | Vance |
| 5,782,776 A | 7/1998 | Hani |
| 5,813,405 A | 9/1998 | Montano, Jr. et al. |
| 6,193,706 B1 | 2/2001 | Thorud et al. |
| 7,578,803 B2 | 8/2009 | Rome et al. |
| 2008/0082051 A1* | 4/2008 | Miller ............ A61M 25/09041 604/164.13 |

(Continued)

*Primary Examiner* — Tuan V Nguyen
*Assistant Examiner* — Chima Igboko
(74) *Attorney, Agent, or Firm* — Brinks Gilson & Lione

(57) ABSTRACT

A wireguide set is provided for changing access between two access sites. The wireguide set includes a wireguide and a catheter. The wireguide passes through one access site while the catheter passes through another access site. The wireguide and catheter are connectable to each other inside the patient's body. Once connected, the catheter can pull the wireguide through the access site of the catheter. The wireguide set may be used to treat peripheral arterial disease occlusions in the lower leg where it is difficult or impossible to gain access through the occlusion from a femoral site.

21 Claims, 2 Drawing Sheets

(56) References Cited

U.S. PATENT DOCUMENTS

2010/0174352 A1\* 7/2010 Van Der Leest  A61B 17/12136
                                                     623/1.11
2010/0312224 A1   12/2010 Atthoff et al.
2014/0005712 A1\*  1/2014 Martin ................. A61B 17/221
                                                     606/200

\* cited by examiner

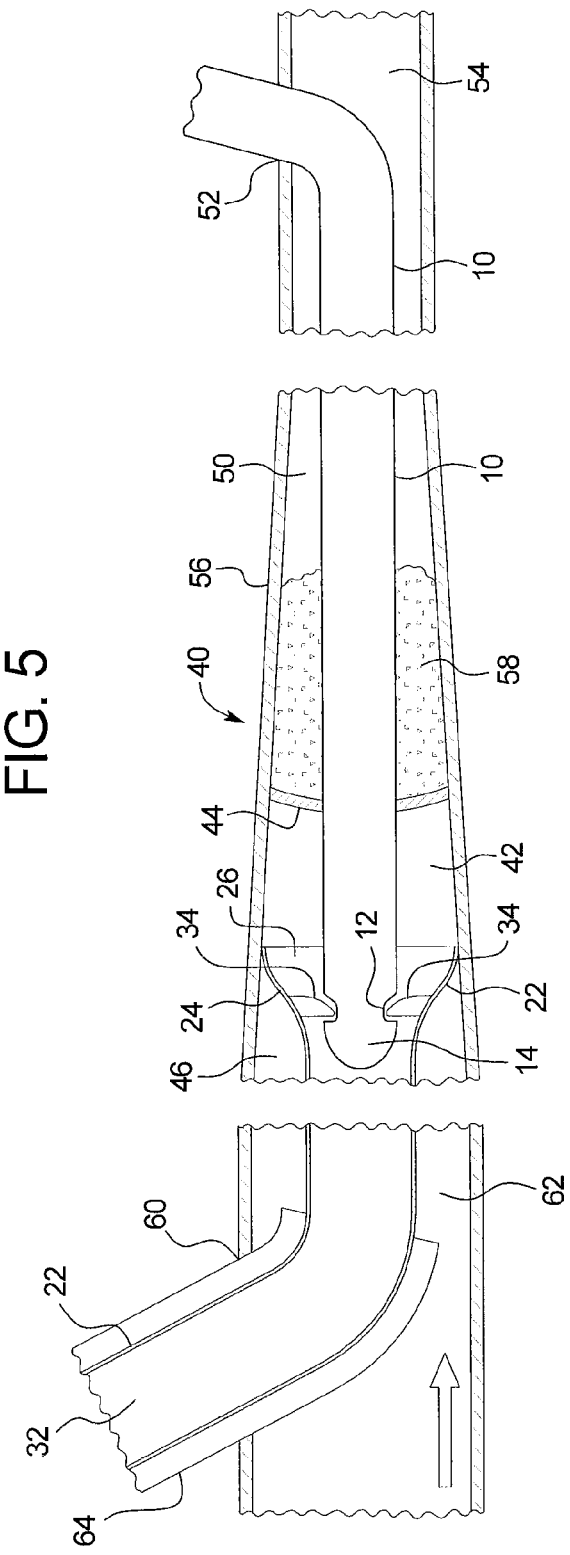

WIREGUIDE SET FOR CHANGING ACCESS SITES

This application claims priority to U.S. Provisional Application No. 61/636,943, filed Apr. 23, 2012, which is hereby incorporated by reference herein.

BACKGROUND

The present invention relates generally to medical devices and more particularly to a wireguide and catheter for changing access to a treatment site from two different access sites.

Minimally invasive medical procedures have become common in the medical profession due to the lower risk and trauma associated with minimally invasive procedures and the lower cost compared to open surgical procedures. Minimally invasive procedures generally involve gaining access to a patient's internal vessel by puncturing the patient's skin, intermediate tissues between the skin and the vessel, and the wall of the vessel. An elongate medical instrument may then be inserted through the access site so that the distal end of the medical instrument is located within the patient's internal vessel, while the proximal end of the medical instrument remains outside the patient's body. The physician may then manipulate the proximal end of the medical instrument outside the patient's body to move and orient the distal end of the medical instrument to a location within the vessel where treatment is needed. Thus, a treatment site within a patient's vessel may be treated from outside the patient's body through a relatively small access site that is located some distance from the treatment site. By contrast, conventional open surgical procedures would require opening the tissues immediately adjacent the treatment site so that the surgeon can gain direct access to the treatment site.

One example of where minimally invasive procedures are commonly used is the treatment of stenoses and other obstructions within vessels using angioplasty techniques. Typically, angioplasty procedures are performed using a balloon-tipped catheter that may or may not have a balloon-expandable stent mounted on the balloon. In general, a physician performs an angioplasty procedure by introducing a balloon catheter into a peripheral artery (commonly one of the leg or arm arteries) and threading the catheter to the narrowed region of the artery. During this stage, the balloon is uninflated and collapsed onto the shaft of the catheter in order to present a low profile which may be passed through the arterial lumens. Once the balloon is positioned at the narrowed region of the artery, the balloon is expanded by pumping a mixture of saline and contrast solution through the catheter to the balloon. As a result, the balloon presses against the inner wall of the artery to dilate it. If a balloon-expandable stent is mounted on the balloon, the balloon inflation also serves to expand the stent and implant it in the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. Alternatively, the balloon catheter may be used to dilate a stenosis without implanting a stent. A balloon-expandable stent or self-expandable stent may then be implanted in the dilated region in a follow-up procedure. If desired, a physician may also dilate the artery and stent a second time after the stent is implanted with a balloon catheter.

In most minimally invasive procedures, a single access site is sufficient to treat a particular condition within a vessel. Although multiple medical instruments may be needed to complete the entire procedure (e.g., angiography catheter, filter, balloon catheter, a stent delivery system, etc.), each of the medical instruments usually access the treatment site through a single access site. Thus, an operation requiring multiple medical instruments can be performed with a single access site by alternately withdrawing and inserting each of the instruments through the access site. This is a significant advantage of minimally invasive procedures because complicated medical procedures involving numerous different instruments can be accomplished while limiting trauma to a single, relatively small access site.

Although most minimally invasive medical procedures use a single access site to minimize trauma and cost, some minimally invasive medical procedures may benefit from the use of two different access sites, where the two access sites are on opposite sides of the treatment site. However, obtaining access to the treatment site from two different access sites can be complicated and time-consuming. Therefore, the inventor believes an improved wireguide set for changing access between two different access sites would be desirable.

SUMMARY

A wireguide set is described for changing access between two different access sites on different sides of a treatment site. The wireguide set includes a wireguide and a catheter. The catheter has a distal opening and a catch in the opening. The wireguide is pushed through the opening in the catheter inside a patient's body so that the catch connects the catheter and the wireguide together. The catheter may then be pulled through the vasculature to pull the wireguide from one access site to another access site. The wireguide set may be particularly useful for treating peripheral arterial disease occlusions in the lower leg.

BRIEF DESCRIPTION OF SEVERAL VIEWS OF THE DRAWINGS

The invention may be more fully understood by reading the following description in conjunction with the drawings, in which:

FIG. 5 is a cross-sectional view of a treatment site being accessed from two different access sites.

DETAILED DESCRIPTION

Figure 1:
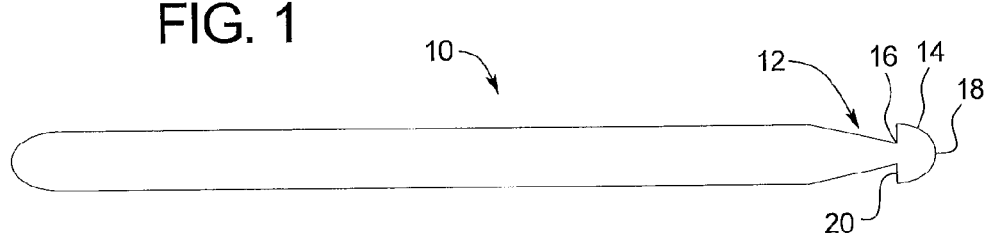
FIG. 1 is a side view of a wireguide.
Figure 2:
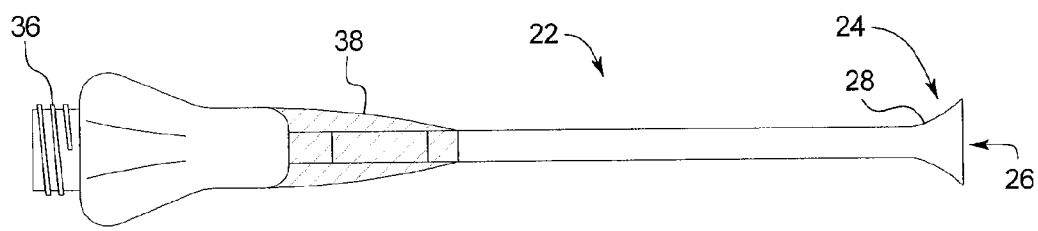
FIG. 2 is a side view of a catheter.

Referring now to the figures, and particularly to FIGS. 1-2, a wireguide set is shown for gaining access to a treatment site 40 from two different access sites 52, 62 on opposite sides of the treatment site 40. The wireguide set includes a wireguide 10 and a catheter 22. As shown in FIG. 1, the wireguide 10 has a circumferential groove 12 near the distal end 14 of the wireguide 10. The circumference of the distal end 14 of the wireguide 10 is larger in size than the groove 12. The groove 12 and distal end 14 of the wireguide 10 may be formed by machining the groove 12 into the wireguide 10 so that the distal end 14 is formed as an integral part of the wireguide 10. However, the distal end 14 may also be a separate member that is welded, soldered, screwed, or otherwise attached to the wireguide 10. If desired, the groove 12 may be tapered from the nominal diameter of the wireguide 10 to the groove's smallest diameter 16 immediately adjacent the distal end 14. The distal end 14 may also be atraumatically rounded at the leading edge 18 and may have a generally lateral edge 20 immediately adjacent the groove 12.

Although the wireguide set may be used for treating other medical conditions, a preferred medical procedure described further below is the treatment of peripheral arterial disease occlusions 40 in the arteries 42 of the lower leg. However, the wireguide set may be especially useful for treating severe occlusions 40 where it is difficult to push a wireguide through the occlusion 40 from the upstream side of the occlusion 40. For example, the Rutherford classification scale is one system for describing the different stages of peripheral arterial disease. Severe claudication corresponds to a Rutherford Stage 3 occlusion 40. Accordingly, it is believed that the wireguide set may be particularly useful for Rutherford Stage 3 or worse occlusions 40, since it may be difficult or impossible to gain access through severe occlusions 40 like this from a femoral access site 60. In addition, the wireguide set may be even more useful for chronic total occlusions 40 where the artery 42 is practically completely occluded. In these situations the shape and structure of the occlusion 40 makes it nearly impossible to push a wireguide through the occlusion 40 and typically requires a wireguide from a femoral access site 60 to be pushed around the outside of the occlusion 40, and possibly through the tissues of the vessel wall.

For peripheral arterial disease occlusions 40 in the lower leg, it is preferred that the diameter of the wireguide 10 be about 0.012" to about 0.016", and the length of the wireguide 10 be at least 250 cm. Most preferably, the diameter of the wireguide 10 is about 0.014", and the length of the wireguide 10 is about 300 cm. Preferably, the diameter of the distal end 14 of the wireguide 10 is about the same as the nominal diameter of the wireguide 10, and the smallest diameter 16 of the groove 12 is about 0.004" to about 0.008" less than the diameter of the distal end 14. Most preferably, the smallest diameter 16 of the groove 12 is about 0.008" and about 0.006" less than the diameter of the distal end 14.

Figure 3:
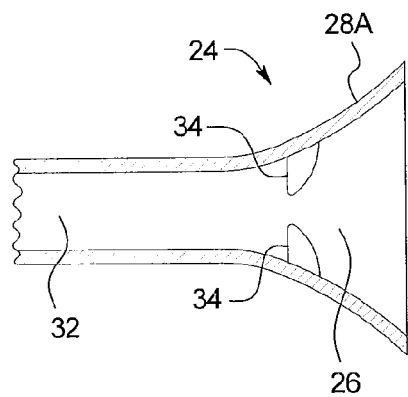
FIG. 3 is an enlarged cross-sectional view of the distal end of the catheter.
Figure 4:
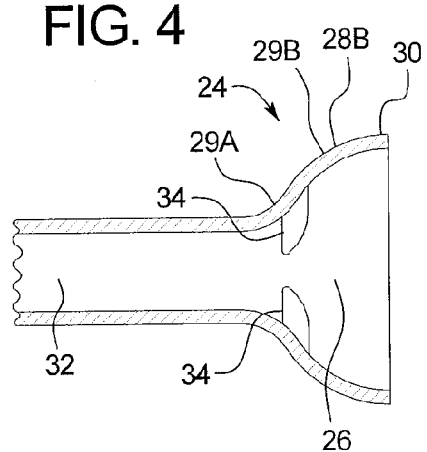
FIG. 4 is an enlarged cross-sectional view of another embodiment of the distal end of the catheter.

As shown in FIG. 2, the catheter 22 has a flared distal end 24. As shown in FIGS. 3-4, the flared distal end 24 defines an opening 26 inside of the flared distal end 24. The shape of the flared portion 28 and the internal opening 26 may vary if desired. For example, as shown in FIG. 3, the flared portion 28A may be concave as viewed from the outside. Alternatively, as shown in FIG. 4, the flared portion 28B may transition from a small concave section 29A at the proximal side to a lengthier convex section 29B along the distal side. The very end of the distal end 24 may also have a length 30 at the largest outer surface of the distal end 24 that extends parallel to the longitudinal axis of the catheter. This may be desirable to make the distal end 24 more atraumatic. It may also be desirable for the flared portion 28 to have the shape of a straight cone. The opening 26 may extend only within the flared portion 28 of the distal end 24 or may extend axially through the catheter 22 so that the opening 26 forms the distal portion of a wireguide lumen 32. Although the catheter 22 may have a solid shaft and an opening 26 only at the distal end 24, it is more preferable for the catheter 22 to have a wireguide lumen 32 in communication with the distal opening 26 so that the catheter 22 can be guided through a vessel with the aid of a wireguide. The catheter 22 also includes a catch 34 within the opening 26.

The catch 34 may extend along only a portion of the circumference of opening 26, but it may be more desirable for the catch 34 to form an internal ring 34 that extends around the entire circumference of the opening 26. The catch 34 may be located within the flared portion 28 of the distal end 24 or may be located within a constant diameter portion of the opening 26 in communication with the wireguide lumen 32.

The catch 34 is made out of a material that is flexible so that it can be deflected by the distal end 14 of the wireguide 10. However, once the groove 12 of the wireguide 10 receives the catch 34 as shown in FIG. 5, the catch 34 must be sufficiently rigid to resist separation of the wireguide 10 and catheter 22 while the catheter 22 pulls the wireguide 10 through a vessel. Preferably, the catch 34 and the distal end 14 of the wireguide 10 are sized so that the catch 34 and distal end 14 interfere about 0.004" to about 0.010", or most preferably about 0.006", when the distal end 14 is pushed through the catch 34. One material that may be used for the catch 34 is silicone, which may be attached to the catheter 22 with an adhesive. Alternatively, the catch 34 may be made from the same class of material as the catheter 22 but with a lower durometer than the catheter 22. For example, the catheter 22 and the catch 34 may be made from nylon, with the durometer of the catheter 22 being about 72 D to about 95 D, and the durometer of the catch 34 being about 25 D to about 55 D. An advantage of making the catheter 22 and the catch 34 from the same class of material, like nylon, is that the catch 34 can be heat bonded to the catheter 22 without requiring an adhesive for bonding.

The catheter 22 may also have a fitting 36 at the proximal end if desired so that a physician can inject or withdraw fluids from the catheter 22. For example, contrast solution could be injected through the catheter 22 to perform an angiography to determine the proper location for the catheter 22. The catheter 22 may also be provided with a strain relief 38 to prevent kinking at the proximal end near the fitting 36. Although the flared portion 28 may be formed in various ways, one way to form the flare 28 is to use a thermoplastic material for the catheter 22 and mold the distal end 24 by heating the thermoplastic material. For treating occlusions 40 in the lower leg, it is preferable for the operable length of the catheter 22 to be about 135 cm to about 175 cm long. It should be understood that this length excludes proximal end portions 36, 38 that are not intended to be inserted into a patient's body. The diameter of the flared distal end 24 is also preferably about 2 mm to about 2.75 mm. Thus, when treating occlusions 40 in the lower leg, the flared distal end 24 may be positioned within the vasculature 56 so that it fills a majority of the diameter of the vasculature 56. It is even more preferable for the flared distal end 24 to fill at least about 75% of the diameter of the vasculature 56, and most preferable to fill at least about 90% of the diameter of the vasculature 56.

Turning to FIG. 5, the wireguide set may be particularly useful for treating occlusions 40, such as chronic total occlusions 40, in the arteries 42 of the lower leg. Chronic total occlusions 40 typically have a hard, calcified cap 44 on the upstream side 46 of the occlusion 40. When a chronic total occlusion 40 like this is located in one of the arteries 42 below the femoral artery 62, such as the anterior tibial, posterior tibial, peroneal and popliteal, it can be particularly difficult and/or traumatic to pass a wireguide through the occlusion 40 from the upstream side 46 using a femoral access site 60. Therefore, in the preferred method of treatment using the wireguide set, access through the occlusion 40 is first obtained from the downstream side 50 using a pedal access site 52. Typically, pedal access 52 is gained through an artery 54 on the top of the foot or through an artery 54 in the ankle. In general, access to any artery 54 in the foot is considered to be pedal access 52.

Once a pedal access site 52 is established, the wireguide 10 is pushed upstream through the vasculature 56. At the treatment site 40, the downstream side 50 of the occlusion 40 is typically a softer, gel-like mixture 58 compared to the calcified cap 44. Thus, the wireguide 10 can more easily penetrate the soft portion 58 of the downstream side 50 of the occlusion 40. At the backside of the calcified cap 44, the wireguide 10 breaks through the cap 44 to obtain access across the cap 44. The wireguide 10 is able to more easily break through the cap 44 in this procedure because of the downstream direction of penetration, and because of the relatively short distance between the pedal access site and the location of the occlusion 40 in the lower leg, which increases column strength, or pushability, of the wireguide 10.

A second access site 60 is also established in the femoral artery 62. Typically, an introducer sheath 64 is used at the femoral access site 60 to feed instruments, like the catheter 22, through the femoral access site 60. The catheter 22 is pushed downstream through the vasculature 56 until the flared distal end 24 is at a location upstream from the occlusion 40. In positioning the flared distal end 24, the physician preferably takes into account the tapering shape of the vasculature 56 and positions the flared distal end 24 so that it fills at least a majority of the diameter of the vasculature 56. This makes it possible to feed the distal end 14 of the wireguide 10 into the distal opening 26 of the catheter 22 without the wireguide 10 inadvertently passing by the outside of the catheter 22. The location where the catheter 22 can be positioned to fill the majority of the diameter of the vasculature 56 can be determined by the physician using an angiography, which will generally show the physician the changing shape of the vasculature 56 along its length. In addition, the physician may use the catheter 22 itself for the angiography by injecting contrast solution through the lumen 32 of the catheter 22. Although it may be sufficient to position the catheter 22 so that the flared distal end 24 fills at least 50% of the diameter of the vasculature 56, it may be more desirable to position the catheter 22 so that the flared distal end 24 fills at least about 75% of the diameter, or at least about 90% of the diameter.

The catheter 22 may be positioned either before or after the wireguide 10 penetrates the occlusion 40. When the occlusion 40 being treated is a chronic total occlusion 40, there may be less concern about blocking blood flow for an extended period of time as a result of the flared distal end 24 filling most of the diameter of the vasculature 56, since the occlusion 40 is already blocking practically all of the blood flow through the vasculature 56. This may also be true of occlusions 40 that are Rutherford Stage 3 and worse. Thus, it is possible that it may be desirable to position the catheter 22 before the wireguide 10 penetrates the occlusion 40. Once the catheter 22 is positioned and the wireguide 10 has penetrated the treatment site 40, the wireguide 10 is pushed through the opening 26 and catch 34 of the catheter 22 until the groove 12 of the wireguide 10 receives the catch 34 of the catheter 22. The catheter 22 may then be pulled upstream through the femoral artery 62 while the catheter 22 pulls the wireguide 10 upstream with the catheter 22. Thus, as described above, the interference between the distal end 14 of the wireguide 10 and the catch 34 must be sufficient to resist separation of the catheter 22 and the wireguide 10 has the catheter 22 pulls the wireguide 10 upstream.

At the femoral access site 60, the catheter 22 may be pulled completely out from the femoral access site 60, which also pulls the distal end 14 of the wireguide 10 through the femoral access site 60. Importantly, the length of the wireguide 10 is selected so that the wireguide 10 remains positioned through the occlusion 40 while the wireguide 10 extends through the femoral access site 60. Thus, the wireguide 10 may now be used to guide other medical instruments through the femoral access site 60 to the treatment site 40 to treat the occlusion 40. For example, it may be desirable to treat the occlusion 40 with a balloon catheter and a self-expanding stent delivery system. However, medical devices like these are typically too large to be used through a pedal access site 50 and are usually used through a femoral access site 60. Thus, the wireguide set allows occlusions 40 in the lower leg arteries 42 to be treated from a femoral access site 60 where initial access through the occlusion 40 is difficult or not possible from the femoral access site 60.

Although the wireguide set may be particularly useful for treating occlusions in the anterior tibial artery, posterior tibial artery, peroneal artery and popliteal artery using a first access site into the pedal artery and a second access site into a femoral artery, it may also be desirable to use the wireguide set to treat other arteries, and it may also be desirable to use other access sites with the wireguide set. For example, the anterior tibial artery, posterior tibial artery, peroneal artery, and popliteal artery could be treated with a first access site into the anterior tibial artery, posterior tibial artery or peroneal artery and with a second access site into the femoral artery. Likewise, the first access site could be any artery below the knee while the second access site could be any artery in the leg above the knee. While the vasculature being treated is preferably in or below the knee and above the foot, it is also possible that the wireguide set may be used to treat other vasculature regions in the body. For example, arteries above the knee in the leg, in the arm, in the neck or head, and in the torso may be treated with the wireguide set. In the broadest sense, the wireguide set may be useful for any treatment site in the body where access must be changed between two different access sites.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A method for treating a peripheral arterial disease occlusion in a vasculature below a femoral artery, comprising:

gaining access to said vasculature at a first access site below a popliteal artery;

pushing a wireguide through said first access site and upstream through said vasculature, said wireguide comprising a circumferential groove adjacent a larger distal end portion;

gaining access to a femoral artery at a second access site;

pushing a catheter through said second access site and downstream through said femoral artery, said catheter comprising a flared distal end and an elastic catch within an opening defined by said flared distal end;

positioning said catheter within said femoral artery or said vasculature such that said flared distal end fills a majority of a diameter thereof at a location upstream from said occlusion in said vasculature;

pushing said wireguide upstream through said occlusion;

pushing said distal end portion of said wireguide through said opening and said catch of said catheter until said groove of said wireguide receives said catch of said catheter;

pulling said catheter upstream through said femoral artery, said catheter thereby pulling said wireguide upstream through said femoral artery with said catheter;

pulling said catheter completely out from said second access site, said wireguide thereby being pulled through said second access site while remaining positioned through said occlusion.

2. The method according to claim 1, wherein said vasculature comprises an anterior tibial artery, posterior tibial artery, peroneal artery, or popliteal artery.

3. The method according to claim 1, wherein said occlusion is a Rutherford Stage 3 or worse occlusion.

4. The method according to claim 3, wherein said occlusion is a chronic total occlusion.

5. The method according to claim 1, further comprising determining said location where said catheter is positioned to fill said majority of said diameter from an angiography.

6. The method according to claim 1, wherein said flared distal end fills at least about 75% of said diameter.

7. The method according to claim 6, wherein said flared distal end fills at least about 90% of said diameter.

8. The method according to claim 1, wherein said flared distal end has a diameter of about 2 mm to about 2.75 mm.

9. The method according to claim 1, wherein said catch of said catheter and said distal end portion of said wireguide are sized to interfere with each other about 0.004" to about 0.010".

10. The method according to claim 1, wherein said flared distal end of said catheter comprises a length at a largest outer surface of said flared distal end that extends parallel to a longitudinal axis of said catheter.

11. The method according to claim 1, wherein an operable length of said catheter is about 135 cm to about 175 cm long.

12. The method according to claim 1, wherein an overall length of said wireguide is at least about 250 cm long.

13. The method according to claim 1, wherein said catch is made of silicone.

14. The method according to claim 1, wherein said catch is made from a nylon having a durometer of about 25D to about 55D, said catheter being made from a nylon having a durometer of about 72D to about 95D, and said catch and said catheter are heat bonded together.

15. The method according to claim 1, wherein gaining access at said first access site comprises gaining access to a pedal artery.

16. The method according to claim 1, wherein gaining access at said first access site comprises gaining access to an anterior tibial artery, posterior tibial artery, or peroneal artery.

17. The method according to claim 1, wherein gaining access at said first access site comprises gaining access to a pedal artery, said vasculature comprises the anterior tibial artery, posterior tibial artery, peroneal artery, or popliteal artery, said occlusion is a Rutherford Stage 3 or worse occlusion, further comprising determining said location where said catheter is positioned to fill said majority of said diameter from an angiography, and wherein said flared distal end fills at least about 75% of said diameter.

18. The method according to claim 17, wherein said flared distal end fills at least about 90% of said diameter, and said flared distal end has a diameter of about 2 mm to about 2.75 mm.

19. The method according to claim 18, wherein said catch of said catheter and said distal end portion of said wireguide are sized to interfere with each other about 0.004" to about 0.010", and said flared distal end of said catheter comprises a length at a largest outer surface of said flared distal end that extends parallel to a longitudinal axis of said catheter.

20. The method according to claim 19, wherein an operable length of said catheter is about 135 cm to about 175 cm long, an overall length of said wireguide is at least about 250 cm long, said catch is made from a nylon having a durometer of about 25D to about 55D, said catheter being made from a nylon having a durometer of about 72D to about 95D, and said catch and said catheter are heat bonded together.

21. The method according to claim 1, wherein said vasculature comprises the anterior tibial artery, posterior tibial artery, peroneal artery, or popliteal artery, said occlusion is a chronic total occlusion, an operable length of said catheter is about 135 cm to about 175 cm long, an overall length of said wireguide is at least about 250 cm long, said flared distal end fills at least about 90% of said diameter, and said flared distal end has a diameter of about 2 mm to about 2.75 mm.

* * * * *